(12) United States Patent
Kandel

(10) Patent No.: US 6,464,729 B1
(45) Date of Patent: Oct. 15, 2002

(54) RECONSTITUTED MINERALIZED CARTILAGE TISSUE

(75) Inventor: Rita Kandel, Toronto (CA)

(73) Assignee: Mount Sinai Hospital Corporation, Toronto (CA)

(*) Notice: Subject to any disclaimer, the term of this patent is extended or adjusted under 35 U.S.C. 154(b) by 0 days.

(21) Appl. No.: 09/068,233

(22) PCT Filed: Nov. 5, 1996

(86) PCT No.: PCT/CA96/00729

§ 371 (c)(1), (2), (4) Date: Sep. 29, 1998

(87) PCT Pub. No.: WO97/17430

PCT Pub. Date: May 15, 1997

Related U.S. Application Data

(63) Continuation-in-part of application No. 08/706,625, filed on Sep. 6, 1996, now abandoned.
(60) Provisional application No. 60/007,279, filed on Nov. 6, 1995.

(51) Int. Cl.[7] ............................................... A61F 2/28
(52) U.S. Cl. .................. 623/23.63; 623/915; 623/919; 435/372
(58) Field of Search ........................... 623/23.72, 23.76, 623/23.63, 13.11, 11.11, 915, 919, 920, 923, 925; 435/41, 70.3, 325, 363, 366, 372

(56) References Cited

U.S. PATENT DOCUMENTS

| | | |
|---|---|---|
| 3,703,575 A | 11/1972 | Thiele |
| 4,356,261 A | 10/1982 | Kuettner |
| 4,642,120 A | 2/1987 | Nevo et al. |
| 4,757,017 A | 7/1988 | Cheung |
| 4,846,835 A | 7/1989 | Grande |
| 4,904,259 A | 2/1990 | Itay |
| 4,996,154 A | 2/1991 | Gabriels, Jr. |
| 5,037,656 A | 8/1991 | Pitt et al. |
| 5,041,138 A | 8/1991 | Vacanti et al. |
| 5,053,050 A | 10/1991 | Itay |
| 5,067,962 A | 11/1991 | Campbell et al. |
| 5,160,490 A | 11/1992 | Naughton et al. |
| 5,226,914 A | 7/1993 | Caplan |
| 5,231,169 A * | 7/1993 | Constantz et al. .......... 530/356 |
| 5,282,859 A | 2/1994 | Eisenberg et al. |
| 5,294,446 A | 3/1994 | Schlameus et al. |
| 5,326,357 A | 7/1994 | Kandel |

(List continued on next page.)

FOREIGN PATENT DOCUMENTS

| | | |
|---|---|---|
| EP | 0175286 A3 | 3/1986 |
| EP | 90108381.6 | 3/1990 |
| WO | WO90/12603 | 11/1990 |
| WO | WO93/19168 | 9/1993 |
| WO | PCT/CA96/00729 | 9/1993 |

OTHER PUBLICATIONS

T. Kimura et al. in Urist, M. R., "Clinical Orthopaedics and Related Research", No. 186, Jun. 1984, PA, US pp. 231–239.

(List continued on next page.)

Primary Examiner—Bruce Snow
Assistant Examiner—Brian E. Pellegrino
(74) Attorney, Agent, or Firm—Merchant & Gould, P.C.

(57) ABSTRACT

A biological material comprising a continuous layer of cartilaginous tissue reconstituted in vitro which contains components associated with cartilage mineralization. The biological material may be cultured with a mineralizing agent to form a mineralized biological material. The mineralized biological material is characterized by having a biochemical composition and physiological organization substantially similar to the deep and contiguous calcified cartilage zones of articular cartilage found in animals in vivo. Methods for preparing the biological materials and methods of using the biological materials are described.

11 Claims, 11 Drawing Sheets

U.S. PATENT DOCUMENTS

| | | | |
|---|---|---|---|
| 5,656,450 A | * 8/1997 | Boyan et al. ............... | 435/68.1 |
| 5,716,413 A | 2/1998 | Walter et al. | |
| 5,723,331 A | 3/1998 | Tubo et al. | |
| 5,863,297 A | 1/1999 | Walter et al. | |
| 5,962,325 A | * 10/1999 | Naughton et al. .......... | 435/395 |

OTHER PUBLICATIONS

Zimmermann et al., Cell Differentiation and Development, 31, (1990) 11–22.
Aydelotte and Kuettner, Conn. Tiss. Res., 18:205, 1988.
Zanetti et al., J. Cell Biol., 101:53, 1985.
Poole et al., J. Anat., 138:13, 1984.
Urban and Bayliss, Biochem. Biophys. Acta., 992:59, 1988.
Brown et al., Conn. Tiss. Res., 24:157, 1990.
Schneiderman et al., J. Orthop. Res., 4:393, 1986.
Lane and Brighton, Arth. Rheum., 17:235, 1974.
Morales et al., J. Biol. Chem., 259:6720, 1984.
Manning and Bonner, Arth. Rheum., 10:235, 1967.
Horwitz and Dorfman, J. Cell Biol., 45:434, 1970.
Green, Clin. Orthop. Rel. Res., 75:248, 1971.
Von der Mark et al., Nature, 267:531, 1977.
Solursh, Am. J. Med. Gen., 34:30, 1989.
Watt and Dudhia, Differentiation, 38:140, 1988.
Van Kampen and Veldhuijzen, Exp. Cell. Res., 140–440, 1982.
Delbruck et al., Conn. Tiss. Res., 15:155, 1986.
Thompson et al., Exp. Cell. Res., 157:483, 1985.
Bassleer et al., In Vitro, 22:113, 1986.
Cheung, In Vitro Cell. Dec. Biol., 21:353, 1985.
Guo et al., Conn. Tiss. Res., 19:277, 1989.
Aulthouse et al., In Vitro Cell & Dev. Biol., 25:659, 1989.
Solursh, J. Cell. Biochem., 45:258, 1991.
O'Driscoll et al., Trans. Orthop. Res., 37:125, 1991.
Nakahara et al., Bone, 11:181, 1990.
Amiel et al., Conn. Tiss. Res., 18:27, 1988.
Kuettner et al., J. Cell. Biol., 93:751, 1982.
Macklis et al., In Vitro Cell Develop. Biol., 21:180, 1985.
Goldberg and Kolibas, Conn. Tissue Res., 24:265, 1990.
Yannas, Collagen, 3:87.
Benya & Shaffer, Cell., 30:215, 1982.
Franzen et al., Differentiation, 36:199, 1987.
Solursh, Development and Diseases of Cartridge and Bone Marrow, Alan R. Liss Inc., 1987.
Billings et al., Acta. Orthop. Scand., 61:201, 1990.
Schwartz et al., InVitro, 18:254, 1982.
Jennings et al., Cell. Biol. Int. Rep., 7:149, 1983.
Hale et al., In Vitro Cell. Biol. & Dev. Biol.., 22:597, 1986.
Trippel et al., J. Bone & Joint Surgery, 1990:816.
Robinson et al., Calcif. Tissue Int., 46:246, 1990.
Rudolf Lemperg, Virchows Arch. Abt. A Path. Anat. 352, 1–13, 1971.
Oegema et al., In: Kuettner, K. ed., Articular Cartilage and Osteoarthritis, pp. 319–331, 1992.
Brittberg et al., The New England Journal of Medicine, 331:889–895, 1994.
Leboy et al., The Journal of Biological Chemistry, 264:17281–17286, 1989.
Arsenault and Grynpas, Calcif. Tissue Int. (1988) 43:219–225.
Flygare et al., Acta Odontol Scand 51 (1993), pp. 183–191.
Tervonen et al., Acta Radiologica 32 (1991) Fasc. 5, pp. 389–392.
Oegema, T.R. Jr. and Thompson, R.C. in Articular Cartilage and Osteoarthritis ed. Kuettner et al., pp. 319–331, 1992.
Muller–Gerbl et al., J. Anat. 154:103, 1987.
Quarto et al., J. Cell Biol. 110:1379, 1990.
Poole et al., Anat. Rec. 224:167, 1989.
Hough, A.J. et al., Arthritis and Allied Conditions, ed McCarty, D.J., pp. 1571, 1989.
Thompson et al., J. Bone Surg. 73A:990, 1991.
Vellet et al., Radiology 178:271, 1991.
Ali, S.Y. et al. Fed. Proc. 32:1494–1498, 1971.
Lorenteon, R. et al., Acta. Orthop. Scand. 52:684, 1981.
Einhorn, T.A. et al., J. Orthop Research 3:160, 1985.
Walker et al., J. Orthop Research 13:4, 1995.
Okihana, H. et al., Histochemical J 25:166, 1993.
Nakagawa et al., Calcif Tissue Int., 53:127–134, 1993.
Kato, Y. et al., Proc. Natl. Acad. Sci USA 85:9552–9556, 1988.
Glaser J.H. et al., Journal of Biological Chemistry, 256:12607, 1981.
Gerstenfeld L.C. et al., Journal of Cell Biology, 112:501, 1993.
Hascall, V.C. et al., Journal of Biological Chemistry, 251:3511–3519, 1976.
Bruckner, P. et al., Journal of Cell Biology, 109:2537–2545, 1989.
Wardale, J.R. and Duance, V.C., J. Cell. Sci. 105:975–984; 1993.
Kandel et al., Biochem Biophys. Acta. 1053:130, 1990.
Streuli and Bissell, J. Cell Biol. 110:1405, 1990.
Buck and Horwitz, Ann. Rev. Cell Biol. 3:179, 1987.
Bhatnagar and Qian, 38th Annual Meeting of the Orthopedic Research Society 17:106, 1992.
Boyle, J. et al.,Osteoarthritis and Cartilage 3:117–125, 1995.
Whyte, M.P., Alkaline phosphatase: physiological role explored in hypophosphatasia In Peck WA (ed) Bone and Mineral Research, 6th Ed. Elsevier Science Publishers, Amsterdam, 1989:175–218.
Lovell, T.P. and Eyre, D.R. Trans. Orthop. Res. Soc. 13:511; 1988..
Yoon, K., Golub, E.E., Rodam, G.A. Alkaline phosphatasecDNA transfected cells promote calcium and phosphate deposition. In Glimcher, M.J., Liam, J.B. (eds.) Proceedings of the Third International Conference on the Chemistry and Biology of Mineralized Tissues. Gordon and Breach Science Publishers, New York, 1989; 643–652.
Xu, Y. et al., J. Rheum. 21(5):912–919; 1994.
Iwamoto, M. et al; Dev. Biol. 136:500–507; 1989.
Wu, L.N.Y. et al.; J. Biol. Chem. 264(35):21346–21355, 1989.
Wuthier, R.E. Mechanism of matrix vesicle mediated mineralization of cartilage. ISI Atlas Sci. Biochem 1:231–241; 1988.
Oegema, T.R. Jr., Thompson, R.C. Cartilage–Bone Interface (Tidemark), In Brandt, K. ed. Cartilage Changes in Osteoarthritis, Indiana School of Medicine publication. Basel: Ciba–Geigy; 1990; 43–52.
Nishida, Y. et al.; Osteoarthritis and Cartilage 2:43–49; 1994.
Silbermann, M. et al.; Bone 8:117–126; 1987.
Shaklee, P.N. and Conrad, H.E., J. Biol. Chem. 260:16064–16067; 1985.
Gannon, J.M. et al., J. Orthop. Res. 9:485–494; 1991.
Korver, G.H.V. et al.; Matrix 10:394–401; 1990.
Mitrovic, D.R. and Darmon, N. Osteoarthritis and Cartilage 2:119–131, 1994.
Plaas. A.H.K. and Sandy, J.D. Matrix 13:135–147; 1993.
Database Medline File Server SFN Karlsruhe Abstract 91197702, Marles et al, XP002026296 and International Journal of Experimental Pathology vol. 72, pp 171–182, Apr. 1991.

* cited by examiner 28  14

S  E  S  E  S  E
   II    I     X

US 6,464,729 B1

RECONSTITUTED MINERALIZED CARTILAGE TISSUE

This application is the national stage of international application PCT/CA96/00729 filed on Nov. 5, 1996 (WO 97/17430), and which claims the benefit of U.S. Provisional Application 60/007,279 filed on Nov. 6, 1995 and continuation-in-part of Ser. No. 08/706,625 filed on Sep. 6, 1996, now abandoned.

FIELD OF THE INVENTION

The present invention relates to a biological material enriched for components of mineralized cartilage tissue; a mineralized biological material; methods for producing the biological materials; and methods of using the biological materials.

BACKGROUND OF THE INVENTION

Articular cartilage is a specialized tissue found at the end of articulating bons. It is responsible for the distribution of load resistance to compressive forces, and the smooth gliding that is part of joint function. Articular cartilage is joined to its underlying subchondral bone by a zone of calcified cartilage. The calcified cartilage zone is involved in the distribution of force across the joint. The calcified zone forms after secondary ossification and acts like a growth plate during maturation (Oegema Jr. T R and Thompson R C in Articular Cartilage and Osteoarthritis ed. Kuettner K. et al., pp. 319–331, 1992). Its thickness is in part a function of weight bearing as Muller-Gerbl et al. (J. Anat. 154:103, 1987) have shown. In that study they demonstrated that the percentage of cartilage consisting of calcified cartilage is constant and varies between individuals between 3 to 8.8% of the cartilage thickness (Quarto et al., *J Cell Biol* 110:1379, 1990).

Little is known about the composition of the calcified cartilage and the metabolism of chondrocytes within and immediately above the calcified cartilage zone. In vivo, the cells in this region have alkaline phosphatase activity. While the major collagen is type II, type X collagen is also present. Cartilage in the calcified zone contains about half the proteoglycans found within mature articular cartilage deep zones. Researchers have also reported the presence of osteonectin as well as a unique protein seen only in the calcified zone. The mineral present in the calcified zone varies between species, but shows the characteristic 1.67 calcium-to-phosphate ratio of hydroxyapatite (Oegema et al. in Articular Cartilage and Osteoarthritis, ed. Kuettner K. et al. pp. 319, 1992). The process of calcification has been found to be very complex, involving different interacting matrix molecules and careful regulation at the cellular level through a complex multi-component system which involves many cellular, hormonal, and physicochemical processes (Poole et al. Anat. Rec. 224:167, 1989).

Experimental studies have suggested that the calcified cartilage plays a role in the pathogenesis of the joint disease osteoarthritis. Remodelling of the calcified cartilage with reduplication of the tidemark (the interface between the calcified and non-calcified cartilage) is characteristic of osteoarthritis (Hough A J et al., in Arthritis and Allied Conditions, ed McCarty D J pp. 1571, 1989). It has been postulated that is possible that changes at the osteoarticular junction may contribute to the development of osteoarthritis. In support of this concept Thompson et al. (J. Bone Surg. 73A:990, 1991), using an acute transarticular damage dog model, observed that the dogs develop cartilage degeneration over time if the calcified cartilage and subchondral bone are damaged. This may be relevant to the pathogenesis of osteoarthritis in humans as MRI studies have shown that up to 72% of individuals, who injure their joints, will have subchondral fractures without cartilage damage (Vellet et al., Radiology 178:271, 1991).

Metabolic changes have been identified in osteoarthritis cartilage that suggest involvement of the deep and/or calcified cartilage in this disease. Increased numbers of matrix vesicles and matrix vesicle associated enzymes occur in osteoarthritic cartilage (Ali, S. Y. et al. Fed. Proc. 32:1494–1498, 1971; Lorenteon, R. et al., Acta. Orthop. Scand. 52:684, 1981; and, Einhorn T A et al, J. Orthop Research 3:160, 1985). In addition, chondrocytes isolated from osteoarthritic cartilage show increased synthesis of type X collagen (Walker et al. J. Orthop Research 13:4, 1995).

Study of the calcified cartilage zone has been hampered, in part, by the lack of an in vitro culture system. Although many types of in vitro mineralizing chondrocyte culture systems have been described, these cultures use either growth plate chondrocytes (Okihana H et al., Histochemical J 25:166, 1993; Nakagawa et al., Calcif. Tissue Int. 53:127, 1993; Kato Y., et al., Proc. Natl. Acad. Sci. USA 85: 9552, 1988), embryonic chondrocytes, or embryonic growth plate chondrocytes; cells whose function in vivo is to form bone (Glaser J H et al., Journal of Biological Chemistry, 256:12607, 1981; Gerstenfeld L C et al., Journal of Cell Biology, 112:501, 1993; Hascall V C et al., Journal of Biological Chemistry, 251:3511, 1976; Bruckner P et al., Journal of Cell Biology, 109:2537, 1989). The tissue formed by these cells is not well suited to the study of articular cartilage mineralization as the cartilage serves as a template for bone formation. The cells in the epiphyseal plate cartilage go through a series of cytological changes as they progress through to calcification. In addition, they are surrounded by small amounts of matrix which will be permeated by vascular channels (Poole et al. Anat. Rec. 224:167, 1989). In contrast, the calcified zone of adult cartilage appears to be hyaline cartilage that undergoes mineralization and does not usually undergo vascular invasion unless there is an underlying disease process. Therefore, it is not appropriate to extrapolate observations generated from these mineralizing cultures to the calcified articular cartilage.

U.S. Pat. No. 5,326,357 to the present inventor, describes a reconstituted cartilage tissue characterized by a continuous layer of cartilage tissue having a substantial extracellular matrix and possessing zones similar to those found in animal cartilage in vivo, and methods for preparing the reconstituted cartilage tissue.

SUMMARY OF THE INVENTION

The present inventor has generated an in vitro culture system which mimics the deep articular cartilage and adjacent calcified cartilage zone of articular cartilage. The cultured mineralized cartilaginous tissue contains calcium apatite mineral, matrix vesicles, Type X collagen and it has alkaline phosphatase activity. Polydisperse proteoglycans are synthesized by the chondrocytes in the mineralized cartilage tissue. The proteoglycans have a larger hydrodynamic size than the proteoglycans synthesized by articular chondrocytes in reconstituted non-mineralized cartilage in culture.

Broadly stated the invention relates to a biological material comprising a continuous layer of cartilaginous tissue reconstituted in vitro which contains components associated with cartilage mineralization. The invention also broadly contemplates a mineralized biological material characterized by having a biochemical composition and physiological organization substantially similar to the deep and contiguous calcified cartilage zones of articular cartilage found in animals in vivo.

Chondrocytes from the mid and superficial zones of articular cartilage tissue may be cultured on top of the biological material of the invention to produce a reconstituted mineralized cartilaginous tissue which comprises the mineralized biological material of the invention; and a mid and superficial non-mineralized layer adjacent to and contiguous with the mineralized biological material. The superficial and mid non-mineralized layers have a biochemical composition and physiological organization similar to the mid and superficial zones respectively, of articular cartilage found in animals in vivo. Therefore, the reconstituted mineralized cartilage tissue is substantially similar to articular cartilage tissue in vivo.

The invention also relates to a process for producing the biological material of the invention comprising isolating chondrocytes from the deep zone of cartilage tissue; forming a layer of the chondrocytes on a substrate, and; culturing the chondrocytes in growth media under suitable conditions so that the chondrocytes accumulate matrix and form cartilaginous tissue which is enriched with components associated with cartilage mineralization.

The process may additionally comprise the steps of culturing the chondrocytes or cartilaginous tissue in the presence of a mineralizing agent, to form a continuous layer of a mineralized biological material characterized by having a biochemical composition and physiological organization substantially similar to the deep and contiguous calcified cartilage zones of articular cartilage found in animals in vivo.

In the alternative, the process of the invention may optionally comprise the steps of culturing chondrocytes isolated from the mid and superficial zones of articular cartilaginous tissue on top of the cartilaginous tissue in the presence of a mineralizing agent to produce a reconstituted mineralized cartilage tissue which has a deep mineralized layer, and mid and superficial non-mineralized layers.

The invention further relates to a mineralized biological material comprising a continuous layer of mineralized cartilaginous tissue having a biochemical composition and physiological organization substantially similar to the deep and contiguous calcified cartilage zones of articular cartilage found in animals in vivo, obtained by (a) isolating chondrocytes from the deep zone of articular cartilage tissue; forming a layer of the chondrocytes on a substrate; and (b)(i) culturing the chondrocytes in growth media under suitable conditions so that the chondrocytes accumulate matrix and form cartilaginous tissue, and culturing the cartilaginous tissue in the presence of a mineralizing agent, or (ii) culturing the chondrocytes in growth media in the presence of a mineralizing agent.

The chondrocytes in the biological materials or reconstituted mineralized cartilaginous tissue may be transformed with recombinant vectors containing an exogenous gene encoding a biologically active protein which corrects or compensates for a genetic deficiency. Therefore, the invention also contemplates a mineralized biological material or reconstituted mineralized cartilaginous tissue wherein chondrocytes in the mineralized biological material or reconstituted mineralized cartilaginous tissue are transformed with recombinant vectors containing an exogenous gene encoding a biologically active protein which corrects or compensates for a genetic deficiency.

The invention still further relates to a system for testing a substance that affects calcification of articular cartilage tissue comprising: culturing a biological material, mineralized biological material, or reconstituted mineralized cartilaginous tissue of the invention in the presence of a substance which is suspected of affecting calcification, and determining the biochemical composition and/or physiological organization of tissue generated in the culture, with the biochemical composition and/or physiological organization of the biological material, mineralized biological material, or reconstituted mineralized cartilaginous tissue cultured in the absence of the substance. The substance may be added to the culture, or the chondrocytes in the biological materials or reconstituted mineralized cartilaginous tissue may be genetically engineered to express the substance i.e. the chondrocytes may serve as an endogenous source of the substance.

The invention still further relates to a method of using the biological materials and reconstituted mineralized cartilage tissue of the invention to test pharmaceutical preparations for efficacy in the treatment of diseases of the joint and to a method of using the biological materials and reconstituted mineralized cartilaginous tissue of the present invention as an implant to replace or repair damaged or deficient cartilage. The invention also contemplates using the biological materials of the invention in gene therapy.

The invention also contemplates a method of replacing or repairing damaged or deficient cartilage in a joint of a patient comprising implanting a mineralized biological material or reconstituted mineralized cartilaginous tissue of the invention in the joint of the patient. Methods for enhancing healing of a bone fracture in a patient are contemplated which comprise inserting a mineralized biological material or reconstituted mineralized cartilaginous tissue of the invention into the site of a fracture.

These and other aspects of the present invention will become evident upon reference to the following detailed description and attached drawings.

DESCRIPTION OF THE DRAWINGS

The invention will be better understood with reference to the drawings in which.

DETAILED DESCRIPTION OF THE INVENTION

Figure 1A:
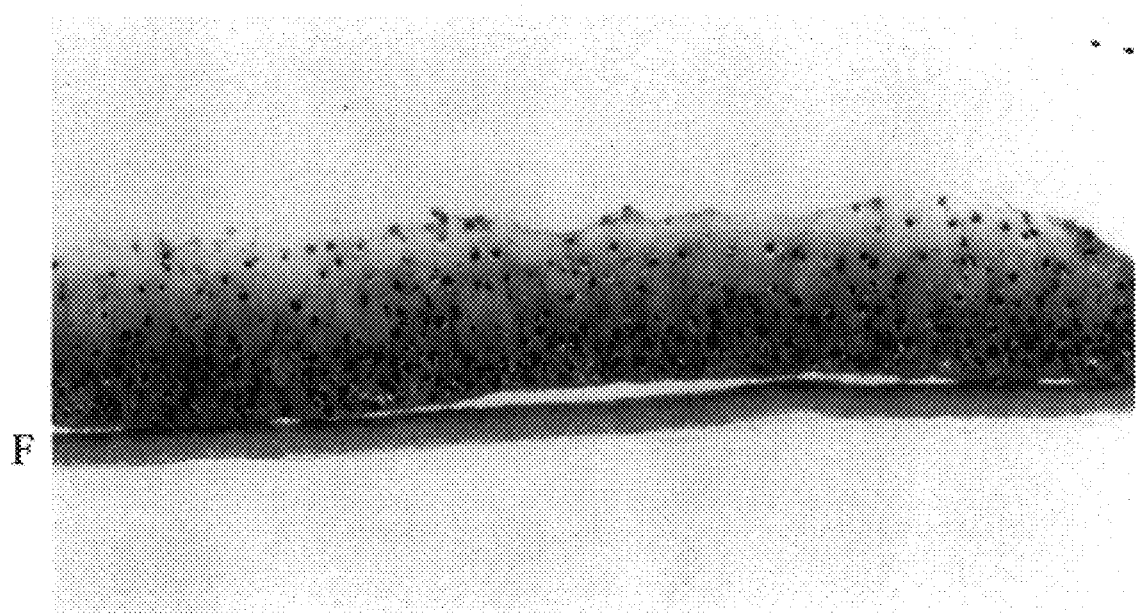
FIG. 1A is a photomicrograph showing the histological appearance of formalin fixed and paraffin embedded chondrocyte cultures harvested at two weeks.

As hereinbefore mentioned, the present invention relates to a biological material comprising a continuous layer of cartilaginous tissue reconstituted in vitro which contains components associated with cartilage mineralization. In particular, it contains matrix vesicles, type X, type I and type II collagens, and it is enriched for chondrocytes with alkaline phosphatase activity. The cells in the biological material synthesize large sulphated proteoglycans and they have a larger hydrodynamic size than proteoglycan synthesized by non-mineralizing articular chondrocyte cultures.

The invention also relates to mineralized biological material having a biochemical composition and physiological organization substantially similar to the deep and contiguous calcified cartilage zones of articular cartilage found in animals in vivo. The mineralized biological material is characterized by having mineral deposits both adjacent to the chondrocytes and within the territorial matrix away from the cells. The mineral deposits form in relationship to matrix vesicles. Electron diffraction demonstrates that the mineral deposit crystals are composed of calcium hydroxyapatite. Alkaline phosphatase activity is detected during mineralization.

The invention also relates to a method for producing a biological material of the invention comprising isolating chondrocytes from the deep zone of articular cartilage tissue; forming a layer of the chondrocytes on a substrate, culturing the chondrocytes in growth media under suitable conditions so that the chondrocytes accumulate matrix and form cartilaginous tissue which is enriched with components associated with cartilage mineralization. The chondrocytes or cartilaginous tissue may be additionally cultured in the presence of a mineralizing agent, to form a continuous layer of mineralized cartilaginous tissue having a biochemical composition and physiological organization substantially similar to the deep and contiguous calcified cartilage zones of articular cartilage found in animals in vivo.

The chondrocytes used in the method of the invention may be isolated from articular cartilage from animals, preferably humans, bovines, ovines, rabbits, most preferably humans. The chondrocytes may be isolated from adult or fetal tissue. In one embodiment of the invention, the chondrocytes are isolated from the metacarpal-carpal joints of calves.

Chondrocytes which are in the deep zone of articular cartilage are preferably isolated. Such chondrocytes may be obtained by isolating the lower 5–25%, preferably 15% of the articular cartilage tissue.

In a preferred embodiment of the invention, cells with an alkaline phosphatase activity of at least about fourfold greater than that detected in the same number of cells obtained from the entire cartilage, are used to establish the cultures in the method of the invention. For example, cells with an alkaline phosphatase activity of at least 2 $\mu$M PNP/hr/$\mu$g DNA, most preferably at least 14 $\mu$M PNP/hr/$\mu$g DNA, may be used to establish the cultures in the method of the invention.

The chondrocytes may be isolated by sequential enzyme digestion techniques, such as those described in Kandel et al, Biochem. Biophys. Acta. 1035:130, 1990. For example, the cartilage may be treated with 0.5% protease followed by 0.04% baterial collagenase.

In accordance with the method of the invention a layer of chondrocytes is formed on a substrate. Suitable substrates include bone, engineered biomaterials and porous tissue culture inserts, for example filter inserts. The substrate is optionally coated with an attachment factor. Attachment factors are known in the art, see for example, Streuli and Bissell, J. Cell. Biol. 110:1405, 1990 and Buck and Horwitz, Ann, Rev. Cell Biol. 3:179, 1987. Examples of attachment factors include type I collagen, type II collagen, type IV collagen, a synthetic peptide of a segment of collagen, preferably a fifteen amino acid sequence $^{766}$GTPGPQ-GIAGQRGVV$^{780}$ which is present in the $\alpha$1 chain of collagen (Bhatnagar and Qian, 38th Annual Meeting of the Orthopedic Research Society 17:106, 1992), fibronectin, gelatin, laminin, polylysine, vitronectin, cytotactin, echinonectin, entactin, tenascin, thrombospondin, uvomorulin, biglycan, chondroitin sulfate, decorin, dermatan sulfate, heparin, and hyaluronic acid. A preferred attachment factor which may be used in the method of the invention is collagen, most preferably type II collagen. When the substrate is coated it may be air dried and sterilized.

In a preferred embodiment of the invention the substrate is a tissue culture insert known as Millicell CM®, (Millipore Corp., Bedford, Mass., U.S.A.), pore size 0.4 $\mu$m, coated with an attachment factor, preferably type II collagen, 0.5 mg/ml 0.012N HCl (Sigma Chemical Co., St. Louis, Mo., U.S.A.).

The chondrocytes are seeded on the substrate at a cell density of about to $1\times10^5$ to $8\times10^6$ cells/cm$^2$, preferably $2\times10^6$ cells/cm$^2$. The chondrocytes seeded on the coated or uncoated substrate are grown in suitable culture conditions. Examples of suitable culture media are known in the art, such as Ham's F12 and/or Dulbecco's modified Eagle's medium (DMEM). Preferably DMEM is used after 4–5 days in culture. The culture medium may contain serum, for example fetal bovine serum in a concentration range of about 2–20% and may further contain growth factors, and optionally ascorbic acid. The culture media is applied above and below the substrate. The cells may be cultured at 37° C. in a humidified atmosphere supplemented with $CO_2$. A cofactor for lysyl oxidase to cross-linked collagen, for example copper sulfate, may be used to retain more collagen and provide thicker cartilage.

In a preferred embodiment of the invention the isolated chondrocytes are grown in Ham's F12 media with 5% fetal bovine serum for 5 days, then the medium is changed to DMEM containing 20% fetal bovine serum, 25 mM Hepes buffer and ascorbic acid (100 $\mu$g/ml, final concentration).

The chondrocytes or cartilaginous tissue enriched for components associated with cartilage mineralization i.e.

biological material may be treated with one or more mineralizing agents which are capable of inducing mineralization. Suitable mineralizing agents include β-glycerophosphate, ATP, and phosphoethanolamine. The concentration of the mineralizing agent used in the method of the invention is selected to provide a desired amount of mineralization. By way of example, the amount of β-glycerophosphate which may be used in the method is about 2.5 to 10 mM, final concentration. The mineralizing agent is generally applied to the cultures after 2 days, preferably 14 days, after initially seeding the chondrocytes. Generally the mineralizing agent is present throughout the culture period to get maximum mineralization. The cells are cultured for an additional 6 weeks to obtain the mineralized biological material described herein. The cells may be cultured for less than 6 weeks (or greater than 6 weeks) to obtain a product which may be suitable for some uses such as transplantation or gene therapy.

The amount of mineralization in the mineralized biological material may be selected using particular culture conditions. For example, smaller mineral deposits occur when the cultures are established with fewer numbers of cells from the deep zone of cartilage, for example, adding increasing numbers of superficial cells back to the deep cultures while still maintaining the same total cell number, decreases the size of mineral deposits. Mineral formation may also be enhanced by including ascorbic acid in the culture medium.

In the cultures, the earliest calcification is seen around chondrocytes and some of these cells appear viable histologically even after six weeks in culture. Minimal amounts of mineralization may occur around occasional single cells during the first weeks of culture. Ultrastructural examination demonstrates that the crystal deposits form in relationship to matrix vesicles. As matrix vesicles are present in the calcified cartilage, this suggests that these cultures may be mimicking the calcification process as it occurs in vivo. The biochemical composition of the mineralized tissue is substantially similar to the calcified zone of articular cartilage tissue. The cells have detectable alkaline phosphatase activity at the initiation of the cultures, and the amount of alkaline phosphatase increases with time during mineralization.

Chondrocytes from the mid and superficial zones of articular cartilage may be cultured on top of the biological material of the invention to generate reconstituted cartilage in vitro that resembles full thickness cartilage in vivo. In an embodiment of the invention, chondrocytes are isolated from the deep zone of articular cartilage and plated in culture as described above. The chondrocytes accumulate extracellular matrix to form cartilaginous tissue. Chondrocytes are then isolated from the mid and superficial zones of articular cartilage and are plated (e.g. at an optimal concentration of $3 \times 10^6$ cells/cm$^2$) on the cartilaginous tissue formed by cells from the deep zone. Although cell concentrations as low as $0.2 \times 10^6$ cells/cm$^2$ can be used. The cultures are grown in suitable culture conditions in the presence of a mineralizing agent as described herein. By way of example, the cultures are grown in Hams F12 medium containing 20% fetal bovine serum, and after about five days the medium is changed to DMEM with 20% fetal bovine serum supplemented with 10 mM β-glycerophosphate, 100 µg/ml ascorbic acid, and 25 mM Hepes buffer. The cultures are then maintained for six weeks or longer. This results in a reconstituted mineralized cartilage tissue which has a deep mineralized layer and mid and superficial non-mineralized layers substantially similar to articular cartilage tissue in vivo.

The biological material, mineralized biological material, and reconstituted mineralized cartilage tissue of the present invention can be used as model systems for in vitro studies of cartilage structure, function and development, and the calcification process.

In accordance with one embodiment of the invention, the biological material, mineralized biological material, and reconstituted mineralized cartilage tissue may be used to test substances which affect calcification. A system for testing for a substance that affects calcification of articular cartilage tissue in accordance with the invention comprises culturing a biological material, mineralized biological material or reconstituted mineralized cartilage tissue of the invention in the presence of a substance which is suspected of affecting calcification, and determining the biochemical composition and/or physiological organization of tissue generated in the culture, with the biochemical composition and/or physiological organization of the biological material, mineralized biological material, or reconstituted mineralized cartilage tissue cultured in the absence of the substance.

The substance may be added to the culture or the chondrocytes in the biological materials or reconstituted mineralized cartilage tissue may be genetically engineered to express the substance i.e. the chondrocytes may serve as an endogenous source of the substance. Chondrocytes may be engineered by viral or retroviral-mediated gene transfer to produce a specific substance. The engineered cells are constructed and maintained such that they release the substance into the medium for the desired period of time for the culture.

The system may be used to analyze the effects of substance(s) on different stages of calcification. Effects on cells at very early, intermediate, and late stages of calcification may be evaluated by assessing the biochemical composition and/or physiological organization of the tissue and the mineralization generated in the cultures at various times such as 2, 4, 6 and 8 weeks.

The biochemical composition and/or physiological organization of the tissue generated in the cultures may be assessed using the methods described herein.

In a preferred embodiment of the invention, the biological materials and reconstituted mineralized cartilage tissue of the present invention may be used in the testing of pharmaceutical preparations useful in the treatment of diseases of the joint, for example, osteoarthritis, inflammatory arthropathies, septic arthritis, and crystalline arthropathies.

The biological materials and reconstituted mineralized cartilage tissue of the invention may also be implanted into the joints of patients to replace or repair damaged or deficient cartilage. The biological materials and reconstituted mineralized cartilage tissue can be used in the study and treatment of chondrodysplasias. In addition the biological material can be used to test angiogenic factors as cartilage is normally resistant to vascular infiltration.

It is also contemplated that the biological materials and reconstituted mineralized cartilage tissue of the present invention can be used to enhance healing of bone fractures when inserted into the site of a fracture.

The invention also contemplates using the biological materials and reconstituted mineralized cartilage tissue of the invention in gene therapy. Therefore, recombinant vectors containing an exogenous gene encoding a biologically active protein which is selected to modify the genotype and phenotype of a cell to be infected may be introduced into chondrocytes in the biological materials and reconstituted mineralized cartilage tissue of the invention. An exogenous gene coding for a biologically active protein which corrects or compensates for a genetic deficiency may be introduced into chondrocytes in the biological materials and reconstituted mineralized cartilage tissue. For example, TIMP (tissue inhibitor of metalloproteases) could be introduced into the chondrocytes so that the cells secrete this protein and inhibit the metalloproteases synthesized by chondrocytes locally in diseases such as osteoarthritis and rheumatoid arthritis. A gene could also be inserted to metabolize iron which would be useful in the treatment of thalassaemia. The expression of the exogenous gene may be quantitated by measuring the expression levels of a selectable marker encoded by a selection gene contained in the recombinant vector.

The following non-limiting examples are illustrative of the present invention:

EXAMPLES

The following materials and methods were utilized in the investigations outlined in the examples:

Chondrocyte Culture: The articular cartilage from the metacarpal-carpal joints of calves was exposed and the majority of the cartilage was removed and discarded. The remaining deep articular and calcified cartilage was dissected off the subchondral bone and collected. The chondrocytes were isolated from this tissue using sequential enzyme digestion and plated at $5 \times 10^6$ cells/cm$^2$ on filter inserts (Millipore$^R$ CM) coated with type II collagen as described in U.S. Pat. No. 5,326,357 and Boyle, J. et al; Osteoarthritis and Cartilage 3:117–125; 1995 which are incorporated herein in their entirety by reference. The cells were plated in Hams F12 containing 5% fetal bovine serum, and 25 mM Hepes. After 5 days the medium was changed to Dulbecco's Modified Eagle's Medium (DMEM) containing 20% fetal bovine serum, 25 mM Hepes and ascorbic acid (100 µg/ml, final concentration). The medium was changed every two to three days and fresh ascorbic acid was added each time. After two weeks in culture β-glycerophosphate (10 mM, final concentration) was added to the medium. In selected experiments, the concentration of β-glycerophosphate was varied from 0 to 10 mM.

Control cultures were established using cells isolated from the entire cartilage as described in U.S. Pat. No. 5,326,357 which is incorporated herein by reference. These cells were maintained in Hams F12 with 20% fetal bovine serum, 25 mM Hepes, and ascorbic acid but they did not receive β-glycerophosphate.

Histological Assessment of Chondrocyte Cultures: The cultures were harvested at varying times up to 8 weeks after plating, fixed in 10% buffered formalin and paraffin embedded. Sections (5 µm) were cut and stained with hematoxylin or eosin to assess the cellularity, toluidine blue to demonstrate the presence of sulphated proteoglycans, or von Kossa to demonstrate the mineralization.

Alkaline Phosphatase Activity: At varying times, the cultures were removed from the filter into Buffer A (0.1% Triton X, 0.2M Tris HCl pH 7.4, 45.7 mM NaCl) and sonicated for 15 sec. on ice. The solution was clarified by centrifugation for 20 min at 4° C. at 700×g and stored at −20° C. until used. Alkaline phosphatase activity was determined by mixing aliquots of the extracts with 0.06M solution of p-nitrophenol phosphate (Sigma Chemical, St. Louis, Mo.) in 0.07M sodium barbitone pH 9.3 (BDH Inc., Toronto, Canada) for 1 hr at 37° C. The reaction was stopped by addition of 50 µl of 1.5N NaOH. The assay was done in 96 well plates and analyzed spectrophotometrically at a wavelength of 405 nm (Titertek Multiskan) (Kato, Y., et al., Proc. Natl. Acad. Sci. 85:9552–9556, 1988). p-Nitrophenol was used to generate the standard curve. Results were normalized against DNA content. All experiments were done in triplicate and repeated at least three times.

DNA Content of Cultures: The cultures were harvested at varying times, and digested with papain and the DNA content measured using Hoescht 33258 dye (Polysciences Inc. Warrington, Pa.) and fluorometry as described previously (Boyle et al., Osteoarthritis and Cartilage, 3:117–125, 1995).

Electron Microscopy: The cultures were harvested at four weeks, fixed in 2% glutaraldehyde in 0.1M sodium cacodylate buffer, post-fixed in 1% osmium tetroxide, dehydrated in graded ethanol series, followed by propylene oxide and embedded in Spurr epoxy resin. Thin sections were cut, stained with lead citrate and uranyl acetate and examined ultrastructurally using a Philips 430 transmission electron microscope. To determine mineral composition, the crystals were examined by selected area electron diffraction and the pattern generated compared to known standards.

Analysis of Collagens in the Matrix: To examine collagen synthesis in these cultures, the chondrocytes were incubated with [$^{14}$C] proline (4 µCi) for 24 hours. The collagens were extracted with pepsin (100 µg/ml in 0.5M acetic acid) [Worthington Biochemical Corp., Freehold, N.J.] for 48 hrs at 4° C. The digestion was stopped by addition of 4× Laemmli buffer. The extract was separated on an 8% SDS-polyacrylamide gel and transferred to nitrocellulose for Western blot analysis and autoradiography. Blots were incubated with antibodies reactive with either type I collagen (Southern Biotechnology Assoc., AL, USA), type II collagen (Southern Biotechnology Assoc., AL., USA), or type X collagen (Gibson, G. Trans. Orthop. Res. 20:28, 1995) overnight. Reactivity was detected using affinity purified goat anti-rabbit IgG antibody conjugated to alkaline phosphatase. Nitroblue tetrazolium and 5-bromo-4-chloro-3-indolylphosphate (NBT/BCIP) were added for substrate and colour reaction (GIBCO BRL, Burlington, Ont, Canada). The blot was then exposed to X-oMat AR film for 1 week.

Analysis of Newly Synthesized Proteoglycans: To analyze proteoglycan biosynthesis in the mineralized cultures, the cultures were incubated with [$^{35}$S] sulphate (1 µCi/well) for 24 hrs prior to harvesting. The proteoglycans were extracted with 4M guanidine HCl in 50 mM sodium acetate, pH 5.8 containing 0.1 M 6-aminohexanoic acid, 50 mM benzamidine HCl, 10 mM EDTA and 5 mM N-ethylmaleimide for 24 hrs at 4° C. The undigested mineral was removed by centrifugation for 5 min at 4° C. The proteoglycan monomer size was examined by Sepharose CL-2B column chromatography (1×100 cm) under dissociative conditions at 4° C. A flow rate of 6 ml/hr was used. The elution profile was analyzed for its partition coefficient, Kav [Kav=(Ve−Vo)/(Vt−Vo)], where Vt=total volume, Vo=void volume, and Ve=elution volume. Vt was determined using [$^{35}$S] SO$_4$ and the void volume determined using dextran sulphate.

Example 1

Characterization of the Mineralized Chondrocyte Cultures

Determination of the Enrichment of Chondrocytes from the Deep Zone: As alkaline phosphatase activity is detected in cells at or above the calcified zone of articular cartilage, this enzyme was used as a marker to assess the enrichment of these cultures with cells from the deep cartilage. Cells with an alkaline phosphatase activity of at least 2 µM PNP/hr/10$^6$ cells, which represented at least a fourfold increase in alkaline phosphatase activity when compared to the alkaline phosphatase activity detected in the same number of cells obtained from the entire cartilage (data not shown), were used to establish the cultures. Cells with alkaline phosphatase activity less than this did not mineralize as well or as rapidly. On average the alkaline phosphatase activity of the cells isolated from the deep layer of cartilage was 4.1±0.8 μM PNP/hr/μg DNA (mean±SE). In contrast the alkaline phosphatase activity of cells isolated from the upper two-thirds of the cartilage which had been dissected off and were not used to establish the cultures was 0.3±0.5 μM PNP/hr/μg DNA (mean±SE) which confirms the enrichment of the cultures with alkaline phosphatase containing chondrocytes.

Figure 1B:
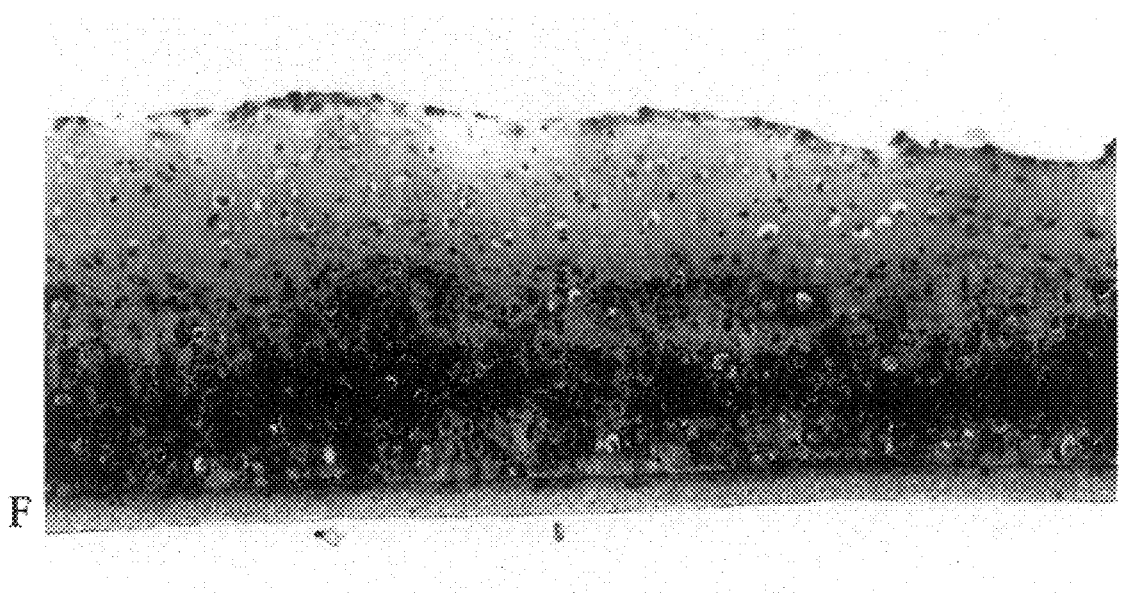
FIG. 1B is a photomicrograph showing the histological appearance of formalin fixed and paraffin embedded chondrocyte cultures which had been grown in the presence of β-glycerophosphate (10 mM) and harvested after eight weeks of culture.

Histological Appearance of the Chondrocyte Cultures: FIG. 1 shows the histological appearance of formalin and paraffin embedded chondrocyte cultures harvested at two (FIG. 1A), and 8 (FIG. 1B) weeks. The filter (F) on which the cells are grown is present and at two weeks the cartilaginous tissue does not show calcification (Von Kossa, magnification ×400).

The chondrocytes during the first two weeks in culture accumulated extracellular matrix to form a continuous layer of cartilaginous tissue which contained sulphated proteoglycans as demonstrated histologically by toluidine blue staining (FIG. 1A). The cells in the lower half of the tissue appeared hypertrophic and were surrounded by large lucanae histologically. Once the tissue had formed, mineralization was induced by the addition of β-glycerophosphate. The calcification occurred rapidly as the deposits could be visualized by phase contrast microscopy within one day of adding β-glycerophosphate in many of the cultures. Histological sections of the cultures demonstrated that the mineralization occurred around single cells in the lower half of the cartilaginous tissue and the extent of mineralization increased over time forming a continuous layer of mineralization (FIG. 1B). Progressive mineralization was not observed histologically when the cultures were maintained in Hams F12 instead of DMEM and when the concentration of β-glycerophosphate was less than 2.5 mM (data not shown). β-glycerophosphate, at concentrations between 2.5 and 10 mM was able to induce mineralization but at a slower rate. Cultures established using chondrocytes obtained from full thickness of cartilage of from just the upper two-thirds of the articular cartilage did not form a continuous layer of mineralized tissue.

Determination of Alkaline Phosphatase Activity of the Cultures: As alkaline phosphatase has been implicated in apatite crystal formation (Whyte, M. P. Alkaline phosphatase: physiological role explored in hypophosphatasia. In: Peck W A (ed.). Bone and Mineral Research, 6th Ed. Elsevier Science Publishers, Amsterdam, 1989:175–218 and Yoon, K.; Golub, E. E.; Rodan, G. A. Alkaline phosphatase cDNA transfected cells promote calcium and phosphate deposition. In: Glimcher M J, Lian J B (eds.) Proceedings of the Third International Conference on the Chemistry and Biology of Mineralized Tissues. Gordon and Breach Science Publishers, New York, 1989;643–652) and because under some culture conditions, chondrocytes can lose this enzyme activity (Xu, Y. et al., J. Rheum. 21(5):912–919; 1994), the cells in culture were assayed for the presence of alkaline phosphatase activity.

Figure 2:
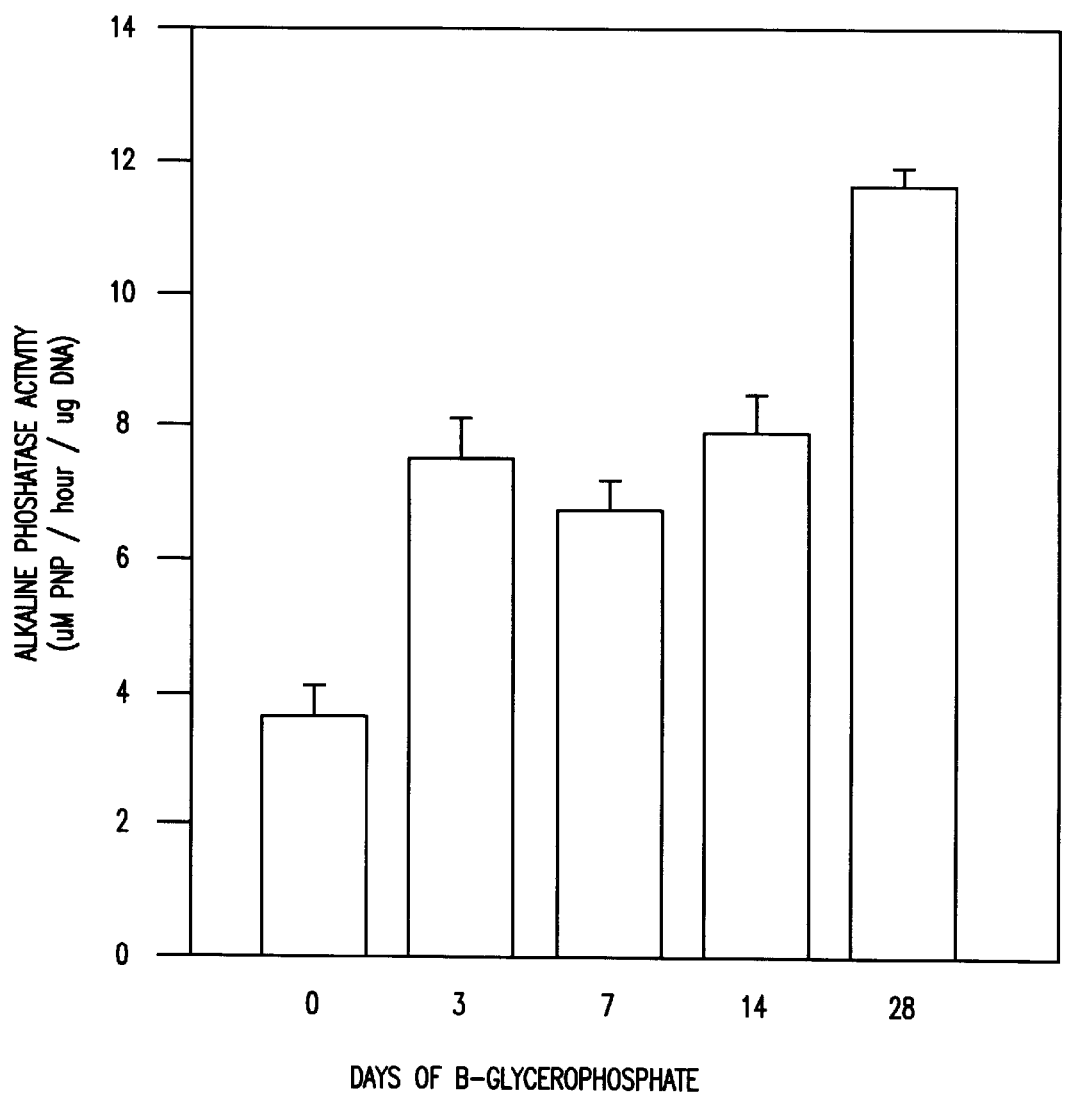
FIG. 2 is a graph showing alkaline phosphatase activity of cultures of deep chondrocytes immediately prior to and during matrix mineralization.

FIG. 2 is a graph showing alkaline phosphatase activity of cultures established from cells from the deep cartilage after two weeks in culture which was just prior to mineralization (day 0) and during matrix mineralization. The results are expressed as the mean±SE of one representative experiment which was repeated three times. Each time point was done in triplicate.

As demonstrated in FIG. 2, the cultures continued to express alkaline phosphatase activity during the culture period. The enzyme activity increased over time. The significance of the increasing alkaline phosphatase activity is unknown but has been shown to occur in other mineralizing cultures (Iwamoto, M. et al; Dev. Biol. 136:500–507; 1989, Wu, L. N. Y. et al; J. Biol. Chem. 264(35):21346–21355, 1989).

Figure 3A:
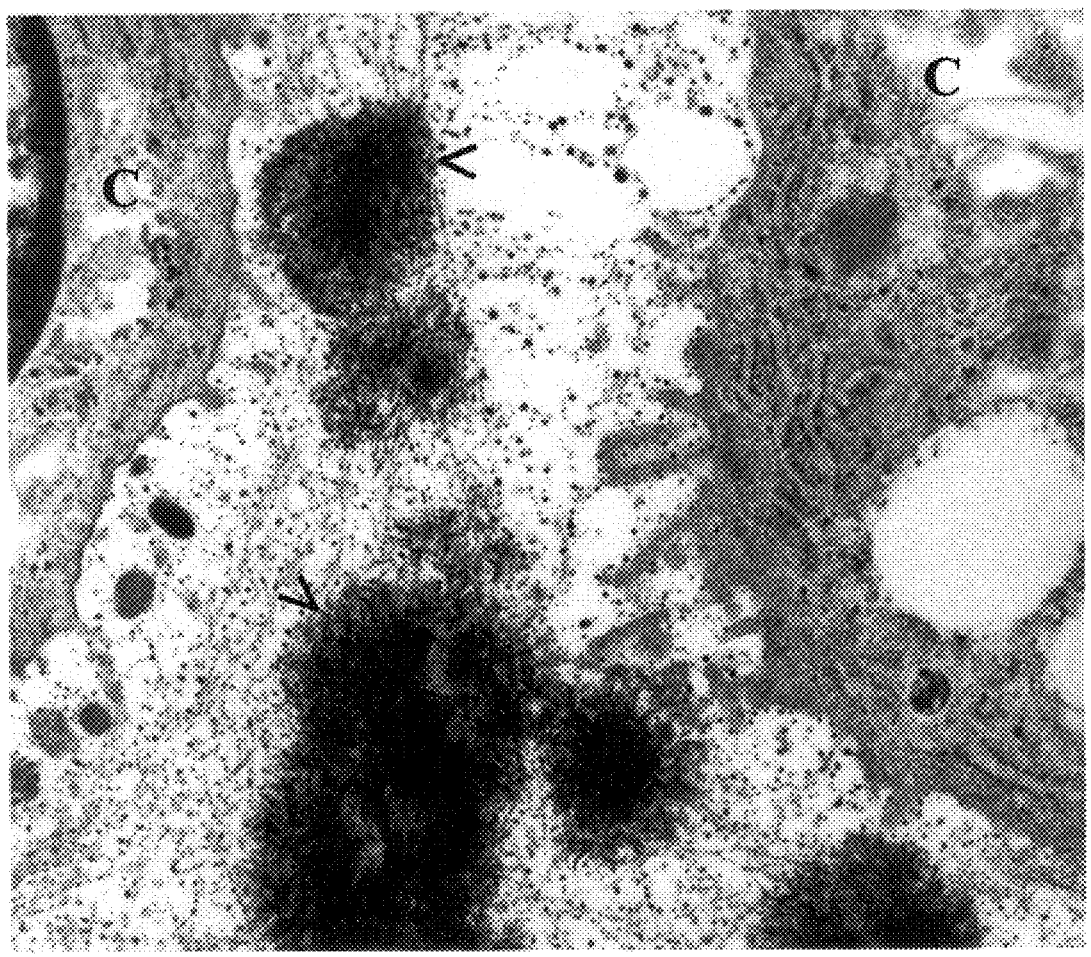
FIG. 3A is an electron micrograph of cartilaginous tissue showing chondrocytes (C) and mineral deposits in the extracellular matrix (<) (lead citrate and uranyl acetate, magnification ×20,000).
Figure 3B:
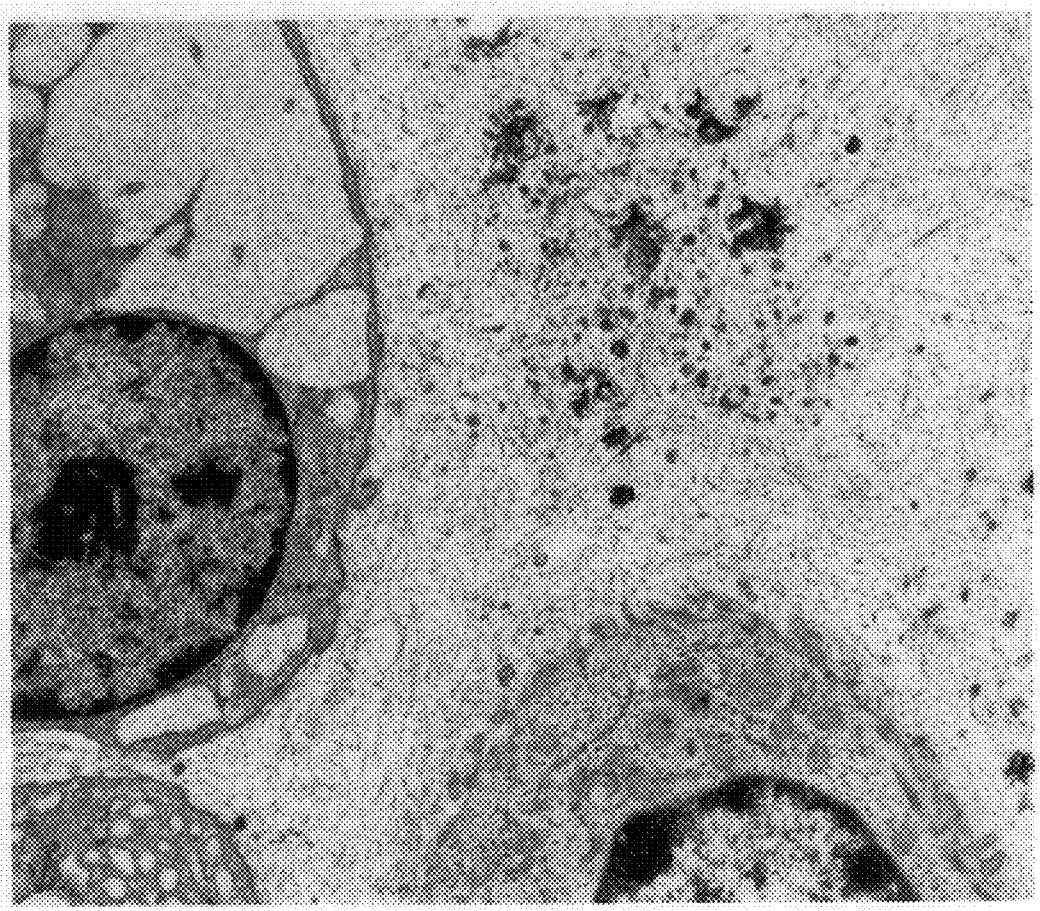
FIG. 3B is an electron micrograph of mineral deposits and matrix vesicles (magnification ×11,000)
Figure 3C:
FIG. 3C is an electron diffraction pattern of crystals which is characteristic of hydroxyapatite.

Ultrastructural Characterization of the Mineral: The mineralized cultures were examined by electron microscopy to determine whether matrix vesicles, which have been implicated as the site of initial crystal formation (Wuthier, R. E. Mechanism of matrix vesicle mediated mineralization of cartilage. ISI Atlas Sci. Biochem. 1:231–241; 1988) are present in the matrix of these cultures. Ultrastructurally, chondrocytes were surrounded by matrix containing collagen and proteoglycans (FIG. 3A). Matrix vesicles were present in the matrix and crystals were seen adjacent to matrix vesicles (FIG. 3B). The crystals had an ultrastructural morphology similar to that of hydroxyapatite crystals. Crystal deposits were seen both adjacent to the chondrocytes and within the territorial matrix away form the cell. Although it is possible that these latter deposits were actually close to cells which were not in the plane of section. The crystals were analyzed by selected area electron diffraction which demonstrated that they were composed of hydroxyapatite (FIG. 3C).

Composition of the Extracellular Matrix: As the extracellular matrix of cartilage contains characteristic macromolecules such as large proteoglycans (aggrecan) and specific types of collagens (Lovell, T. P. and Eyre, D. R. Trans. Orthop. Res. Soc. 13:511; 1988; Oegema, T. R. Jr.; Thompson, R. C. Jr. The zone of calcified cartilage. Its role in osteoarthritis. In: Kuettner, K. eds. Articular Cartilage and Osteoarthritis. New York: Raven Press; 1992:319–331; and Oegema, T. R. Jr.; Thompson, R. C. Cartilage-Bone Interface (Tidemark). In: Brandt, K. ed. Cartilage Changes in Osteoarthritis. Indiana School of Medicine publication. Basel: Ciba-Geigy; 1990:43–52) the matrix composition of the cultures was examined. To assess the types of collagen in the matrix, the matrix was digested with pepsin. The pepsin extracts were subjected to SDS PAGE and either autoradiography or Western blot analysis.

Figure 4A:
FIG. 4A is an autoradiogram of pepsin extracted [$^{14}$C] proline labelled collagens synthesized by chondrocytes after formation of the cartilaginous tissue (14 days) and when the tissue was mineralized (28 days)
Figure 4A:

FIG. 4A shows an autoradiogram of pepsin extracted [$^{14}$C] proline labelled collagens synthesized by chondrocytes after formation of the cartilaginous tissue (14 days) and when the tissue was mineralized (28 days). FIG. 4A, shows bands indicative of type II, type X, and type I collagens in the matrix of the mineralizing chondrocyte culture. Bands suggestive of type XI collagen, which has been detected in the calcified cartilage (Lovell, T. P. and Eyre, D. R. Trans. Orthop. Res. Soc. 13:511; 1988), were also seen on the autoradiogram.

Figure 4B:
FIG. 4B is an immunoblot showing an analysis of collagens extracted from mineralized cultures (day 28) using antibodies reactive with type II collagen (II), type I collagen (I), or type X collagen (X)

The presence of the collagens was confirmed by Western blot analysis. In particular, FIG. 4B shows a Western blot analysis of collagens extracted from mineralized cultures (day 28)(E) using antibodies reactive with type II collagen (II), type I collagen (I), or type X collagen (X). The appropriate purified collagen type was used as a standard (S) for each blot. The types of collagens synthesized by the chondrocytes did not change during matrix mineralization.

Figure 4C:
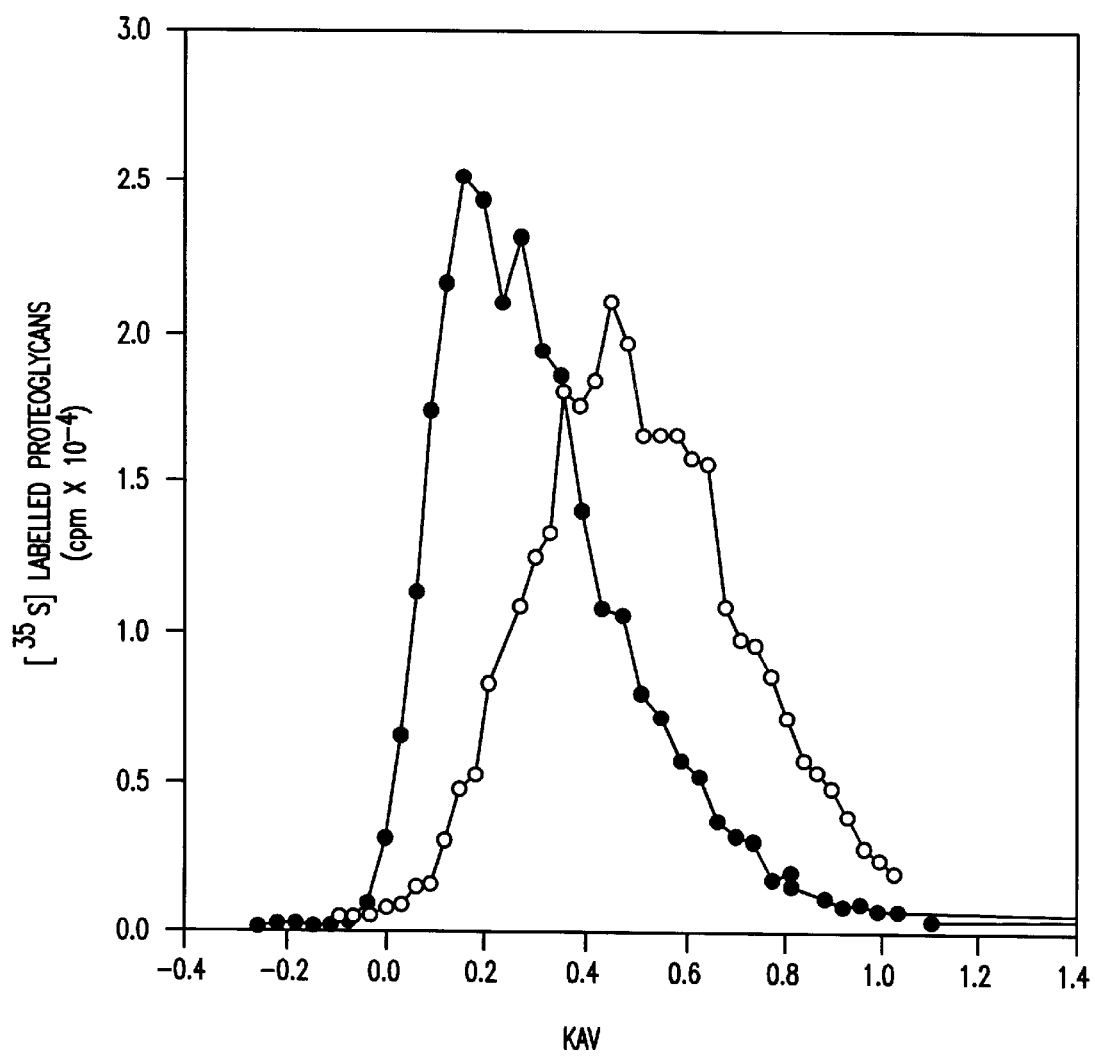
FIG. 4C is a proteoglycan elution profile of newly synthesized proteoglycans extracted from 6 week old mineralized cartilaginous tissue formed in culture (●—●); and 7 week old non-mineralized cartilaginous tissue formed in culture (○—○).

To examine the proteoglycans in the matrix, the [$^{35}$S] SO$_4$ labelled proteoglycans were guanidinium extracted from six week old mineralized cultures. FIG. 4C shows the proteoglycan elution profile or newly synthesized proteoglycans extracted from 42 day old mineralized cultures. [$^{35}$S] SO$_4$ labelled proteoglycan monomer size was determined by Sepharose 2B column chromatography under dissociative conditions. FIG. 4C is a representative profile from an experiment that was repeated five times. Analysis by column chromatography under dissociative conditions demonstrated that the proteoglycans had a large hydrodynamic size (Kav= 0.26±0.03) and were polydisperse (FIG. 4C). These proteoglycans were larger than those synthesized by chondrocytes in non-mineralizing cartilaginous tissue formed in vitro.

The studies illustrated herein describe an articular chondrocyte culture system in which cartilaginous tissue is formed in vitro which can be induced to mineralize. The chondrocytes used to establish these cultures differ from previously described non-mineralizing articular chondrocyte cultures in that the chondrocytes were obtained from the deep zone (lower 15%) of articular cartilage and not from the entire cartilage. This region was selected for cell isolation for two reasons. Firstly, it contains cells with alkaline phosphatase activity, an enzyme which is involved in mineralization (Yoon, K.; Golub, E. E.; Rodan, G. A. Alkaline phosphatase cDNA transfected cells promote calcium and phosphate deposition. In: Glimcher M J, Lian J B (eds.). Proceedings of the Third International Conference on the Chemistry and Biology of Mineralized Tissues. Gordon and Breach Science Publishers, New York, 1989;643–652) and secondly, this region of cartilage can undergo mineralization in vivo indicating that the cells have the potential to synthesize matrix components that favor mineralization under the appropriate conditions.

The results suggest that the mineralizing chondrocyte cultures contain, as has been examined to date, some of the same components as the calcified cartilage (Gannon, J. M. et al, J. Orthop. Res. 9:485–494; 1991; Oegema, T. R. Jr.; Thompson, R. C. Jr. The zone of calcified cartilage. Its role in osteoarthritis. In: Kuettner, K. eds. Articular Cartilage and Osteoarthritis. New York: Raven Press; 1992:319–331; Oegema, T. R. Jr.; Thompson, R. C. Cartilage-Bone Interface (Tidemark). In: Brandt, K. ed. Cartilage Changes in Osteoarthritis. Indiana School of Medicine publication. Basel: Ciba-Geigy; 1990:43–52; and Wardale J. R. and Duance, V. C., J. Cell. Sci. 105:975–984; 1993.), in particular those thought to be involved in cartilage mineralization, such as matrix vesicles, type X collagen and alkaline phosphatase activity (Poole, R. A. et al., Anat. Rec. 224:167–179; 1989). The crystals that formed in these mineralizing cultures were hydroxyapatite, the crystal type present in calcified cartilage. Furthermore, similar to calcified cartilage in vivo, ultrastructural examination demonstrated that the crystal deposits formed in relationship to matrix vesicles. Although the components that have been shown to be involved in mineralization were present in these cultures, β-glycerophosphate was required for the progressive mineralization of the matrix. It has been suggested that the calcification which occurs in the presence of β-glycerophosphate, which is acting as a phosphate donor, may be artefactual (Bruckner, P. et al; J. Cell. Biol. 109:2537–2545; 1989), but this is unlikely to be the situation in these cultures. It was found that the amount of mineralization could be influenced by the number of cells from the deep zone in the culture. If the cultures were established at the same plating density but the deep cells were diluted with increasing numbers of chondrocytes isolated from the superficial zone, this resulted in a decrease in the size of mineral deposits as determined by light microscopic examination of histological sections of the cultures (data not shown). Furthermore although β-glycerophosphate was required, a low concentration of β-glycerophosphate (2.5 mM) was sufficient to induce mineralization.

The chondrocytes in these cultures maintained their phenotype as they synthesized type II collagen and large sulphated proteoglycans, which are characteristic of differentiated chondrocytes. However, type I collagen was also present. This collagen type is not usually detected in normal hyaline (non-mineralized) cartilage and under some culture conditions its synthesis is considered suggestive of chondrocyte dedifferentiation. Immunofluorescence studies have shown that type I collagen is present in the calcified zone of articular cartilage (Wardale, J. R. and Duance, V. C.; J. Cell. Sci. 105:975–984; 1993) so its synthesis by chondrocytes in these cultures likely reflect the cell phenotype. The proteoglycans synthesized by the chondrocytes in mineralizing culture had a larger hydrodynamic size than proteoglycans synthesized by non-mineralizing articular chondrocytes (cells obtained from full thickness cartilage) grown on filter inserts (Boyle, J. et al; Osteoarthritis and Cartilage 3:117–125; 1995). Studies examining the size of proteoglycans extracted from the different layers of articular cartilage from superficial to deep have demonstrated that the hydrodynamic size of the proteoglycans under dissociative conditions were similar but not identical in size in all zones (Korver, G. H. V. et al; Matrix 10:394–401; 1990; Mitrovic, D. R. and Darmon, N. Osteoarthritis and Cartilage 2:119–131, 1994). The hydrodynamic size of the proteoglycans synthesized by chondrocytes in the deep zone of human articular cartilage had a ($K_d$) ranging from 0.18 to 0.22 (Mitrovic, D. R. and Darmon, Osteoarthritis and Cartilage 2:119–131; 1994). The cells of other types of mineralizing cartilage, such as epiphyseal plate chondrocytes and embryonic limb bud cells, have also been shown to synthesize large proteoglycans (Hascall, V. C. et al; J. Biol. Chem. 251:3511–3519; 1976; Plaas, A. H. K. and Sandy, J. D. Matrix 13:135–147; 1993; and Silbermann, M. et al; Bone 8:117–126; 1987). For epiphyseal chondrocytes, the hydrodynamic size of the proteoglycans synthesized varied depending on the location of the cell in the growth plate (Plaas, A. H. K. and Sandy, J. D. Matrix 13:135–147, 1993). Embryonic mesenchymal cells that differentiate into chondrocytes synthesize proteoglycans other than aggrecan (Plaas, A. H. K. and Sandy, J. D.; Matrix 13:135–147; 1993; and Shaklee, P. N. and Conrad, H. E. J. Biol. Chem. 260:16064–16067; 1985). Versican (PG-M) is one the proteoglycans which has been identified and its characterization demonstrated that it has a larger core protein than aggrecan (Plaas, A. H. K. and Sandy, J. D. Matrix 13:135–147; 1993). Versican has also been detected in osteoarthritic articular cartilage (Nishida, Y. et al.; Osteoarthritis and Cartilage 2:43–49; 1994).

In conclusion, the mineralizing articular chondrocytes cultures maintain their phenotype in vivo and should be useful as a model to examine the metabolism of cells from the deep zone of articular cartilage and the mineralization of cartilaginous tissue.

Example 2

Figure 5:
FIG. 5 is a photomicrograph of a formalin fixed, paraffin embedded 49 day old culture showing superficial and midzone chondrocytes cultured on tissue formed by deep cells.

Chondrocytes from the mid and superficial zones of articular cartilage were cultured on top of the mineralized cartilaginous tissue described above. Chondrocytes cultures are grown in Hams F12 medium containing 20% fetal bovine serum as described above, and after about five days the medium is changed to DMEM with 20% fetal bovine serum supplemented with 10 mM β-glycerophosphate, 100 µg/ml ascorbic acid, and 25 mM Hepes buffer. The cultures are then maintained for six weeks or longer. This results in a reconstituted mineralized cartilage tissue which has a deep mineralized layer and mid and superficial non-mineralized layers substantially similar to articular cartilage tissue in vivo. In particular, FIG. 5 is a photomicrograph of 49 day old culture showing superficial and midzone chondrocytes cultured on cartilaginous tissue formed by the deep cells. Cartilaginous tissue is present and mineral deposits are present in the tissue generated by the deep cells only (Von Kossa stain).

Figure 6:
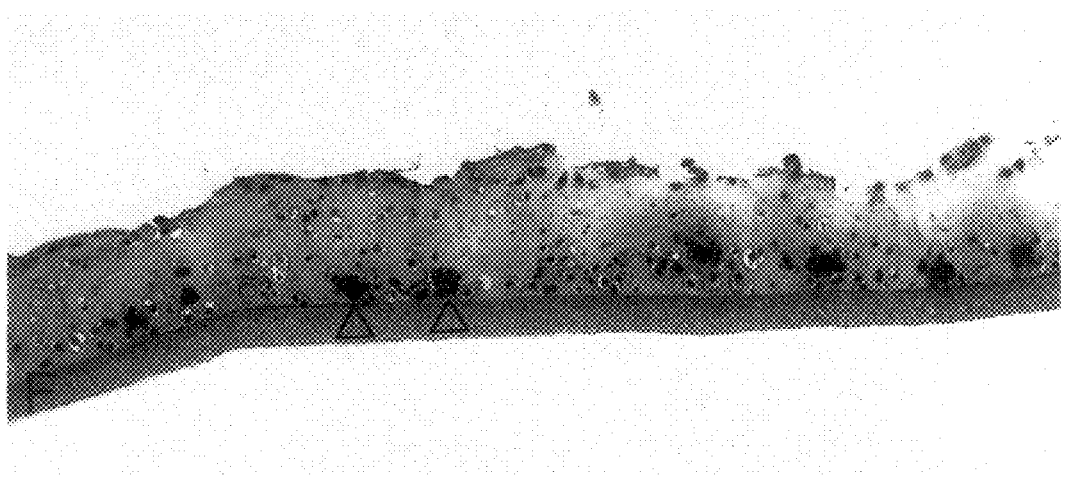
FIG. 6 is a photomicrograph showing the histological appearance of formalin-fixed and paraffin-embedded 22 day old chondrocyte culture, which had been grown in the presence of ATP.

FIG. 6 is a photomicrograph showing the histological appearance of formalin-fixed and paraffin-embedded chondrocyte culture. The cultures have been incubated for 8 days in the presence of ATP, and mineralization (Δ) is seen in the lower zone of the tissue. The filter insert is still present beneath the cartilaginous tissue (F).

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications are herein incorporated by reference in their entirety to the same extent as if each individual publication, patent or patent application was specifically and individually indicated to be incorporated by reference in its entirety.

I claim:

1. A method for producing an isolated mineralized biological material comprising a continuous layer of mineralization comprising chondrocytes having alkaline phosphatase activity and surrounded by matrix containing type I, type II and type X collagens, sulphated proteoglycans having a large hydrodynamic size, matrix vesicles and calcium hydroxyapatite crystal deposits, comprising:

(a) isolating chondrocytes from the lower 15% of animal articular cartilage tissue having an alkaline phosphatase activity of at least 2 $\mu$M PNP/hr/$\mu$g DNA;

(b) forming a layer of the chondrocytes on a substrate wherein the substrate is bone, an engineered biomaterial or a porous tissue culture insert;

(c) culturing the chondrocytes in growth media under suitable conditions so that the chondrocytes accumulate matrix and form cartilaginous tissue which contains components associated with cartilage mineralization, and (d) culturing the cartilaginous tissue in the presence of a mineralizing agent selected from the group consisting of β-glycerophosphate, ATP, and phosphoethanolamine, to form the mineralized biological material.

2. A method as claimed in claim 1 wherein the chondrocytes are isolated by sequential enzyme digestion techniques.

3. A method as claimed in claim 2 wherein the chondrocytes are isolated by treatment with 0.5% protease followed by 0.04% bacterial collagenase.

4. A method as claimed in claim 1 wherein the chondrocytes are seeded on the substrate at a cell density of about $1\times10^5$ to $8\times10^6$ cells/cm$^2$.

5. A method as claimed in claim 4 wherein the chondrocytes are seeded on the substrate at a cell density of about $2\times10^6$ cells/cm$^2$.

6. A method as claimed in claim 1 which further comprises transforming chondrocytes in the mineralized biological material with recombinant vectors containing an exogenous gene encoding a biologically active protein which corrects or compensates for a genetic deficiency.

7. A method as claimed in claim 1 which further comprises after step (c) culturing chondrocytes isolated from the mid and superficial zones of animal articular cartilage tissue on the cartilaginous tissue in the presence of a mineralizing agent to form a material comprising a mineralized biological material comprising a continuous layer of mineralization comprising chondrocytes surrounded by matrix containing type I, type II and type X collagens, sulphated proteoglycans having a large hydrodynamic size, matrix vesicles, and calcium hydroxyapatite crystal deposits, and a mid and superficial non-mineralized layer adjacent to and continuous with the mineralized biological material corresponding to the mid and superficial layers of articular cartilage in vivo.

8. A method as claimed in claim 1 wherein the substrate is a porous tissue culture insert coated with an attachment factor.

9. A method for producing an isolated mineralized biological material comprising a continuous layer of mineralization comprising chondrocytes having alkaline phosphatase activity and surrounded by matrix containing type I, type II and type X collagens, sulphated proteoglycans having a large hydrodynamic size, matrix vesicles and calcium hydroxyapatite crystal deposits, and a mid and a superficial non-mineralized layer adjacent to and continuous with the layer of mineralization comprising:

a) isolating chondrocytes from the lower 15% of animal articular cartilage tissue having an alkaline phosphatase activity of at least 2 $\mu$M PNP/hr/$\mu$g DNA;

b) forming a layer of the chondrocytes on a substrate wherein the substrate is bone, an engineered biomaterial or a porous tissue culture insert;

c) culturing the chondrocytes in growth media under suitable conditions so that the chondrocytes accumulate matrix and form cartilaginous tissue which contains components associated with cartilage mineralization; and d) culturing chondrocytes isolated from the mid and superficial zones of animal articular cartilage tissue on the cartilaginous tissue in the presence of a mineralizing agent selected from the group consisting of β-glycerophosphate, ATP, and phosphoethanolamine, to form the biological material.

10. A method as claimed in claim 9 wherein the chondrocytes are isolated by sequential enzyme digestion techniques.

11. A method as claimed in claim 9 wherein the chondrocytes are seeded on the substrate at a cell density of about $1\times10^5$ to $8\times10^6$ cells/cm$^2$.

* * * * *